United States Patent

Unkrig et al.

(10) Patent No.: US 8,137,980 B2
(45) Date of Patent: Mar. 20, 2012

(54) ON-BOARD CONTROL FOR ANALYTICAL ELEMENTS

(75) Inventors: Volker Unkrig, Ladenburg (DE); Christine Nortmeyer, Mannheim (DE); Carina Horn, Biblis (DE); Michael Marquant, Mannheim (DE); Mihail Onoriu Lungu, Schwegenheim (DE); Joachim Hoenes, Zwingenberg (DE); Holger Kotzan, Ladenburg (DE); Joerg Dreibholz, Altrip (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 13/032,443

(22) Filed: Feb. 22, 2011

(65) Prior Publication Data

US 2011/0177605 A1 Jul. 21, 2011

Related U.S. Application Data

(63) Continuation of application No. 10/962,796, filed on Oct. 12, 2004, now Pat. No. 7,914,752.

(30) Foreign Application Priority Data

Oct. 9, 2003 (DE) .................. 103 46 863

(51) Int. Cl.
*G01N 21/00* (2006.01)
*G01N 27/28* (2006.01)
(52) U.S. Cl. .......... 436/106; 436/95; 436/107; 436/118; 422/68.1; 422/82.05; 422/400; 422/420
(58) Field of Classification Search .................. 422/400, 422/420, 68.1, 82.05; 436/14, 95, 107, 118, 436/106
See application file for complete search history.

(56) References Cited

U.S. PATENT DOCUMENTS

| 3,899,295 A | 8/1975 | Halpern |
| 4,038,148 A | 7/1977 | Miller et al. |
| 5,096,813 A | 3/1992 | Krumhar et al. |
| 5,122,244 A | 6/1992 | Hoenes et al. |
| 5,206,147 A | 4/1993 | Hoenes |
| 5,240,860 A | 8/1993 | Hoenes |
| 5,279,790 A * | 1/1994 | Corey et al. .................. 422/420 |
| 5,286,362 A | 2/1994 | Hoenes et al. |

(Continued)

FOREIGN PATENT DOCUMENTS

DE 2941471 12/1980

(Continued)

OTHER PUBLICATIONS

Maeda, H., et al. "Resazurin as an Clectron Acceptor in Glucose Oxidase-Catalyzed Oxidation of Glucose", Chem. Pharm. Bull:49(5)622-625 (2001).
Gottfried, V., et al., "Temperature effects on photosensitized processes", J. Photochem, Photobiol, B. Biol, 8 (1991) 419-430.

*Primary Examiner* — Robert J Hill, Jr.
*Assistant Examiner* — Dwan A Gerido
(74) *Attorney, Agent, or Firm* — McDonnell Boehnen Hulbert & Berghoff LLP (57) ABSTRACT

The invention concerns a reagent system for the so-called on-board control of analytical elements, in particular test strips, containing an organic N-oxide or a nitroso compound. The invention also concerns analytical elements containing a reagent system for a detection reaction and a reagent system for an on-board control. Furthermore, the invention concerns a method for checking analytical elements in which a reagent system for an on-board control is examined optically or electrochemically with the aid of a measuring instrument for changes which could indicate a stress of the analytical element.

15 Claims, 3 Drawing Sheets

| U.S. PATENT DOCUMENTS | | | | FOREIGN PATENT DOCUMENTS | | |
|---|---|---|---|---|---|---|
| 5,334,508 A | 8/1994 | Hoenes | | DE | 19831519 | 1/2000 |
| 5,344,754 A | 9/1994 | Zweig | | EP | 0826777 | 3/1998 |
| 5,356,782 A | 10/1994 | Moorman et al. | | JP | 09124076 | 5/1997 |
| 5,484,708 A | 1/1996 | Hoenes et al. | | WO | 9209870 | 6/1992 |
| 5,504,011 A | 4/1996 | Gavin et al. | | WO | 0149876 | 7/2001 |
| 6,060,323 A | 5/2000 | Jina | | | | |
| 6,084,660 A | 7/2000 | Shartle | | * cited by examiner | | |

ON-BOARD CONTROL FOR ANALYTICAL ELEMENTS

BACKGROUND OF THE INVENTION

The invention concerns a control reagent system for an analytical element, for example in the form of a test strip and, in particular, a test strip for determining a coagulation parameter which allows a differentiation between functioning analytical elements and non-functioning analytical elements. The invention also concerns corresponding analytical elements and methods for their control.

So-called carrier-bound tests are being used to an increasing extent for the qualitative and quantitative analysis of components of a liquid sample in particular a body fluid from humans or animals. Analytical elements (also referred to as test elements) are used for this where at least one reagent is embedded in a test field consisting of one or more layers, which is brought into contact with the sample. The reaction of sample and reagent results in a change in the analytical element that can be evaluated visually or with the aid of an instrument (usually by reflection photometry or electrochemically). After a test has been carried out the used analytical element is disposed of.

Numerous different types of analytical element are known which differ in their measuring principle (e.g., optical or electrochemical) and the reagents that are used and in their construction and in particular with regard to the arrangement and attachment of the test layers. Strip-shaped analytical elements are of particular practical importance. These analytical elements that are also referred to as test strips are essentially composed of an elongate support layer made of a plastic material on which one or more test fields are attached.

The analytical elements are packaged in primary packaging in the interior of which they are stored until use i.e., until they are removed by the user and a test has been carried out with subsequent disposal. The analytical elements may be packaged individually in their own primary packaging. Analytical element packaging units are commonly used in which a plurality of analytical elements are located in the interior of a common primary packaging. The primary packaging usually contains a desiccant.

The interior of the primary packaging is usually substantially hermetically sealed. Hence, the storage conditions are essentially determined by the environmental conditions in the primary packaging during storage.

Many analytical elements contain reagents which can be damaged by certain storage conditions e.g., temperature, humidity, oxygen, light, etc., which makes them unusable for carrying out a reliable test. Hence, in order to avoid damage it is necessary to store the analytical element packaging unit under certain appropriate conditions recommended by the manufacturer. On the part of the manufacturer, the storage life of the analytical element is guaranteed for a certain period when stored properly.

The use of an analytical element with a damaged reagent can lead to a false test result which may result in a serious misinterpretation of, for example, the state of health of a person. Hence, in the past, various attempts have been made to reduce the risk of using analytical elements with storage damage.

For example, test reagents have been developed that are relatively insensitive to external effects. The aim of another development is to use elaborate primary packaging to minimize external effects on the reagents of the analytical elements. Both solutions are associated with substantially increased manufacturing costs. For safety reasons a relatively short shelf life is stated. As a result, analytical elements can no longer be used after the shelf life date has expired although it is not possible to check whether in fact there have been conditions which could have resulted in damage to the reagents.

Test strips for diagnostic blood examinations are subject to an extensive quality control before sale. Suitable shipping and storage conditions are intensively examined before they are launched on the market and are, for example, described on the packaging or in the package insert. Nevertheless, it cannot be completely excluded that strips are damaged before the expiration date during transport of the goods to the customer or due to incorrect storage by the customer and that there is a risk that false measurements are obtained when they are used.

Improper transport and/or storage conditions can be discovered by measurements using liquid controls which are distributed as additional system components besides the instrument and strips for most so-called point of care systems (PoC systems) that are used decentrally (i.e., outside of special laboratories i.e., for example, in doctor's offices, pharmacies or by the patient at home). Disadvantages of using liquid controls for PoC systems (e.g., for coagulation measurement systems) are their somewhat complicated handling, the costs for using usually two test strips and two control liquids (level 1 & level 2 control) and the fact that although usually strips from the same production lot and packaging are measured with the controls they are, however, inevitably other strips than those with which the blood sample of a patient is in fact examined.

These disadvantages are avoided by an on-board control (abbreviated as OBC in the following) which is integrated into each test strip and does not require an additional test liquid. Systems with on-board controls require no control liquids but work with the same sample liquid from which the parameter to be determined is determined with the measurement system.

A common feature of systems with on-board controls known in the art is that a blood sample is taken up into an analytical element through a capillary channel and is transported by capillary forces to a site of examination within the analytical element. The sample is divided by one or more branches of the capillary system and conveyed into one or more side channels. Reagents are then located in these side channels which constitute the actual OBC.

A common disadvantage of these on-board controls is that the test strips—in addition to the actual measurement channel for the patient sample—require several (usually two) additional channels. After being filled with the same patient blood, measurements are carried out in these additional channels which should give information about the integrity of the strip. This concept results in high manufacturing costs since the individual channels have to be separately provided with different reagents. Furthermore, such control systems require comparatively large sample volumes since, in addition to the actual measurement channel, at least one and usually even several control channels have to be filled with sample. Large sample volumes are regarded as being a particular disadvantage where patients themselves have to regularly obtain the sample i.e., for example, in so-called home monitoring especially in the case of diabetics or patients which have to monitor their own coagulation values since the collection of blood samples by puncturing the skin is painful and even more painful the more blood sample is required. Moreover, multichannel on-board control systems suffer from difficult filling mechanisms since the sample has to automatically penetrate into several channels and fill them.

SUMMARY OF THE INVENTION

It is against the above background that the present invention provides certain unobvious advantages and advancements over the prior art. In particular, the inventors have recognized a need for improvements in on-board control systems for analytical elements.

Although the present invention is not limited to specific advantages or functionality, it is noted that the present invention provides an on-board control system which does not have the disadvantages noted above, especially with regard to manufacturing costs and sample volume, but nevertheless reliably indicates the potential unusability of test elements, especially as a result of improper storage or transport conditions. In particular, damaging humidity and/or temperature stress on the test elements should be detected with the aid of the OBC according to the present invention. Furthermore, the intended OBC should not react too early in order to enable a long storage of the product at room temperature and should enable a good discrimination between intact and defective strips with a high precision.

In accordance with one embodiment of the present invention, a reagent system for the on-board control of analytical elements is provided comprising an organic N-oxide or a nitroso compound.

In accordance with another embodiment of the present invention, an analytical element comprising a reagent system for a detection reaction and the reagent system for the on-board control of analytical elements according to the first embodiment of the present invention is provided.

In accordance with still another embodiment of the present invention, a method for the control of analytical elements is provided comprising examining the reagent system for the on-board control optically or electrochemically with the aid of a measuring instrument for changes which can indicate a stress of the analytical element.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which.

DETAILED DESCRIPTION OF THE INVENTION

The concept according to the present invention, which can also be referred to as a 1-channel on-board control, provides that a reagent zone on a test element which can also be used for the actual measurement of the patient sample, contains a substance which changes when stressed. The change in this substance can result in a degradation product which can either be detected visually or by the instrument provided to measure the test strip. A strip that has been recognized to be defective can for example not be released by the measuring instrument for measuring the patient sample.

The reagent system according to the present invention is suitable for the on-board control of analytical elements. The reagent system contains at least one chemical substance, but typically a mixture of chemical substances. At least one of these substances is suitable for directly or indirectly indicating environmental conditions which could impair the reliability of an analytical element. This property is referred to as an on-board control property. For this purpose, damaging environmental effects such as temperature, humidity, light, oxygen, etc., are utilized to carry out a typically irreversible change in the said substance or with the said substance which enables a subsequent detection of the damaging effects. In this connection it is usually irrelevant to determine the exact type of damaging effects; it is usually sufficient to establish the fact that a damaging effect has taken place.

The reagent system for on-board control can contain other auxiliary substances in addition to the substance which has the actual on-board control function. These may be buffer substances, fillers, film formers and such like which are known to a person skilled in the art in numerous embodiments in connection with reagent formulations for analytical test elements.

In the sense of the invention analytical elements (also referred to as test elements, analytical test elements, test strips, test chips, test devices) are typically suitable for determining analytes or other parameters in liquid samples and more typically in liquid samples of human origin such as blood, serum, plasma, urine and such like. Analytical elements in the sense of the invention typically contain a reagent or reagent system on a support material which generates a detectable signal that is dependent on the analyte to be examined in the sample or on the property of the sample to be examined. Such analytical elements are known to a person skilled in the art in numerous embodiments. Examples are optical or electrochemical test strips for detecting metabolites in blood or sample liquids derived therefrom and in particular for determining glucose, cholesterol and such like. Furthermore, test strips are known which can be used to determine coagulation parameters in a blood sample.

The reagent system that is located on the analytical element and which is responsible for a detectable detection signal for an analyte in the sample or for a property of the sample can typically result in an optically detectable and evaluable measurement signal or a signal that can be detected by electrochemistry. Both variants are known to a person skilled in the art in numerous embodiments.

The reagent system for on-board control according to the invention is typically integrated into the reagent system for the detection reaction. However, it is also conceivable and possible to accommodate reagent systems for the detection reaction and reagent systems for the on-board control in spatially separated zones on an analytical element.

For the typical case that the reagent system for the on-board control is integrated into the reagent system for the detection reaction care must be taken that the reagents do not negatively affect one another.

The reagent system for the on-board control and the reagent system for the detection reaction can be based on the same or on different detection principles. Thus, according to the present invention, it is possible to optically or electrochemically evaluate the on-board control. It is also possible to optically or electrochemically detect the actual detection reaction. It is more typical to electrochemically detect the on-board control as well as the detection reaction. In this connection an optical detection can be carried out visually or by means of an apparatus with the aid of a photometer in which case any methods familiar to a person skilled in the art such as reflection measurement, absorption measurement, transmission measurement, luminescence measurement and such like can be used. In turn, for the electrochemical detection methods such as potentiometry, amperometry, coulometry, chrono-amperometry and such like are suitable.

In particular, an optical change in the on-board control field or detection reagent field can be evaluated with the naked eye without using a measuring instrument. However, it is typical to evaluate the on-board control and the detection field with the aid of a measuring instrument, for example, a photometer or an electrochemical measuring instrument. It is also possible to evaluate the on-board control without a measuring instrument but to evaluate the detection reaction with a measuring instrument.

The reagent formulations for the on-board control and the detection field can be applied to a support of an analytical element using any methods known to a person skilled in the art. In this connection the various reagents can be applied using the same or different methods. Some of the possible methods are for example: application in a liquid form and subsequent drying on or into a support; application as a coating mass by knife coating, slot nozzle coating and the like; and printing processes such as ink-jet printing, screen printing, dispersing, etc. It is also possible to mount reagents already applied to a first support together with this first support on the actual second support of the analytical element and to join them e.g., by gluing, welding, etc.

The on-board control according to the present invention should be able to reliably detect stressed test elements. In this connection stress is understood to mean that test elements have been exposed to environmental conditions which could lead to damage or impairment of the reagents for the actual detection reaction. In the case of analytical elements which are intended to be stored at room temperature in closed cans provided with desiccants or provided with moisture-impermeable foils, stress is, for example, understood as exposure to high temperatures in the closed cans or foils (e.g., during transport to the customer or behind a pane of glass in sunlight) or damp storage (in the case of improperly closed cans after removing test strips or defective foil packaging). Of course, combinations of stress events such as concurrent humidity or elevated temperature can result in damage. In this case it is only important that a stress finally results in an impairment or failure of the detection reagent system. These can indeed be different specific conditions for the various analytical elements. A person skilled in the art knows how he can identify such damaging events for the respective reagent system.

According to the present invention, a stress of the analytical element or of the reagent system for the on-board control results in a—typically irreversible—change in the reagent system of the on-board control. This ensures that damaging environmental effects are also detected when the environmental conditions have in the meantime changed into favourable conditions. For example, a single damaging temperature elevation or a single brief effect of humidity which has resulted in damage can thus be reliably identified.

Surprisingly, it was found that reagents which contain N-oxides or nitroso compounds, in particular, in combination with reducing agents such as sugars, polyalcohols, cysteine-containing proteins, glycine, etc., can be reduced under the same conditions and environmental effects under which an OBC should indicate undesired effects and negative changes of a test strip. The degradation products formed by reduction from the N-oxides or nitroso compounds can be detected in the test strip by suitable, typically electrochemical or optical methods. In particular, if sugars are used as the reducing agents, the redox properties and hence the kinetics of the redox reaction can be adjusted by means of the pH of the reagent.

According to the present invention, the N-oxide resazurin can be a particularly suitable molecule for the described indicator reaction and is thus typical.

The blue resazurin is reduced to the red resorufin (cf., FIG. 1) when stressed under conditions that could damage a test strip (e.g., elevated temperatures, humidity and light) where the reduction takes place especially in the presence of a suitable redox partner, typically those from the reagent formulation. The change, i.e., the decrease in the resazurin concentration with a simultaneous increase in the resorufin concentration can be determined visually by an optical detector in a measuring instrument or by an electrochemical sensor.

In the case of resazurin, glycine can be a very specific reducing agent. A combination of suitable amounts of resazurin and glycine in an OBC reagent is more typical, in accordance with the present invention. A minimum concentration of about 0.01 g/l resazurin is typical, since detection of resazurin is practically very difficult below this concentration. The maximum amount of resazurin should not exceed about 20 mmol/l since otherwise solubility problems can occur. As described above, glycine is not absolutely necessary for the function of the OBC containing resazurin; a concentration of about 250 g/l has proven to be the maximum amount of glycine since solubility problems occur above this amount and glycine may crystallize from the solution which in turn can cause problems when coating the reagent mass and may lead to inhomogeneities in the coated mass.

The remaining resazurin and/or the resorufin that is formed can be quantified for the electrochemical detection of the OBC reaction.

A quantification of resazurin is typical for large changes in concentration and can for example be carried out by electrochemical reduction of the resazurin at a potential of about −700 mV against Ag/AgCl. At this potential the resorufin that is formed is reduced further to dihydro-resorufin (cf., FIG. 1).

If mainly resazurin is present in the OBC reagent (and hence the reagent is not stressed or hardly stressed) a 4-electron transition is provoked which results in a higher current than when mainly resorufin is present whose reduction only leads to a conversion of 2 electrons. The current or charge measured at a predetermined potential and in particular at a typical potential of about −700 mV against Ag/AgCl thus allows deductions to be made about the extent of the temperature and/or humidity stress of the reagent.

Resorufin cannot be quantified by electrochemical (re)oxidation of resorufin to resazurin because the reduction of resazurin to resorufin is irreversible. A reductive detection in the described OBC system only requires that the reduction of resorufin is specifically detected but not the reduction of resazurin which may be present in the reagent. This can, for example, be accomplished by using a specific reduction potential which is typically in the range of about −450 to about −550 mV against Ag/AgCl.

The quantification of resorufin in the described OBC system can be achieved especially well when in a first step the resorufin present in the test strip is converted electrochemically into dihydro-resorufin (referred to as OBC-prepare) and the in situ generated dihydro-resorufin is electrochemically oxidized back to resorufin in a second step (referred to as OBC test in the following). This oxidation reaction typically runs at a potential of about −100 mV against Ag/AgCl.

The intensity and specificity of the OBC test signal can be controlled by the length of the OBC prepare phase.

In addition to the typical resazurin/resorufin system of the present invention, nitroso compounds and, in particular, p-nitrosoanilines are another typical example for a class of substances which can be converted into products which can indicate a possible damage of the test strip under conditions that can damage test strips. p-Nitrosoanilines can, for example, be reduced under conditions which can also damage reagents in a detection reagent. The products (such as phenylenediamines) produced by reduction can also be detected optically or electrochemically. Other nitroso compounds which can be used according to the present invention are described in the following U.S. Pat. Nos: 5,206,147, 5,334,508, 5,122,244 and 5,286,362, the disclosures of which are incorporated herein by reference for their teaching of nitroso compounds. A combination of the nitroso compounds disclosed in these US patents with heteropoly acids, in particular heteropoly acids in a precipitated form according to U.S. Pat. No. 5,240,860, the disclosure of which is incorporated herein by reference, which when stressed formed readily visible heteropoly blue in the presence of reducing agents is typical.

The invention is characterized in more detail by the following examples which describe the advantages and properties of the OBC according to the invention using test strips for coagulation measurements as an example (prothrombin time test or PT test). It is clear to a person skilled in the art that the statements made on the basis of the coagulation test strip example also apply to other types of test strip and in particular to those used for the optical or electrochemical determination of blood glucose, lipids such as cholesterol and HDL cholesterol, triglycerides, etc., for the determination of other coagulation parameters than PT such as aPTT, ACT, ECT, anti-factor Xa tests and also for immunological test elements, in particular chromatography test strips that can be evaluated optically and can be applied to them. Accordingly, in order that the invention may be more readily understood, reference is made to the following examples, which are intended to illustrate the invention, but not limit the scope thereof.

EXAMPLES

Example 1

Two Reagent Formulations Containing Different Reducing Agents for an On-board Control that can be Evaluated Optically

TABLE 1

Formulation for an OBC containing glycine as a reducing agent that can be evaluated optically

| Chemicals | Source | Concentration |
| --- | --- | --- |
| Sucrose | Sigma | 3.2 g/dl |
| Mowiol 4/86 | Clariant GmbH | 1.3 g/dl |
| Keltrol F | Kelco | 2.98 g/ml |
| Glycine | Sigma | 1.35 g/dl |
| HEPES[1] | Sigma | 0.33 mg/ml |
| polyethylene glycol PEG 3,350 | Sigma | 1.33 g/dl |
| bovine serum albumin | Sigma | 0.4 g/dl |
| mega 8 | Sigma | 0.67 mg/ml |
| Resazurin | Riedel de Haen | 0.96 mg/ml |

[1]HEPES: [4-(2-hydroxyethyl)-piperazino]-ethane sulfonic acid

The substances listed in Table 1 are mixed homogeneously and adjusted to a pH of 7.4 with NaOH. The reaction mass obtained in this manner was coated onto a test strip that can be measured by reflection photometry as a reagent tape of 20 mm width and ca. 10 μM thickness.

TABLE 2

Formulation for an OBC containing glucose as a reducing agent that can be evaluated optically

| | pH of the formulation | | | |
| --- | --- | --- | --- | --- |
| | 7.5 | 9 | 10 | 11 |
| Chemical | Amount weighed out in g | | | |
| polyvinylpyrrolidone solution[1] | 7.09 | 7.09 | 7.09 | 7.09 |
| glucose | 1.2 | 1.2 | 1.2 | 1.2 |
| HEPES[2] | 1.25 | — | — | — |
| CHES[3] | — | 1.04 | 1.04 | — |
| CAPS[4] | — | — | — | 1.11 |
| bidistilled water | 7.72 | 7.93 | 7.93 | 7.86 |
| Keltrol F solution[5] | 17.04 | 17.04 | 17.04 | 17.04 |
| BM propiofan 70 D | 5.69 | 5.69 | 5.69 | 5.69 |
| titanium dioxide slurry[6] | 55.32 | 55.32 | 55.32 | 55.32 |
| resazurin | 0.28 | 0.28 | 0.28 | 0.27 |
| hexanol | 0.17 | 0.17 | 0.17 | 0.17 |
| methoxy-2-propanol | 4.25 | 4.25 | 4.25 | 4.25 |

[1]40 g/l polyvinylpyrrolidone (PVP) is scattered into water and restirred for about 30 min.
[2]HEPES: [4-(2-hydroxyethyl)-piperazino]-ethanesulfonic acid.
[3]CHES: 2-(cyclohexylamino)-ethanesulfonic acid.
[4]CAPS: 3-(cyclohexylamino)-1-propanesulfonic acid.
[5]6.8 g/l Keltrol is scattered into water while stirring and restirred for several hours. In order to ensure a complete swelling, the preparation is allowed to stand overnight at room temperature before further use.
[6]15 g titanium dioxide is scattered into 38 ml water while stirring and then homogenized in a dissolver stirrer at a high stirring rate.

The pH of the reagent mass is in each case adjusted to the stated value with sodium hydroxide solution.

The substances listed in Table 2 are mixed homogeneously. The reaction mass obtained in this manner was coated onto a test strip that can be measured by reflection photometry as a reagent tape of 20 mm width and ca. 10 μm thickness.

The reaction rate of the OBC reaction i.e., the conversion of resazurin into resorufin which depends on the environmental conditions can be adjusted by the pH. The more alkaline the pH the more rapid is this conversion and hence the more sensitive is the OBC.

Example 2

Mass Spectroscopic Determination of the Degradation Product after Stress in the Reagent Formulation According to Table 1 from Example 1

In the case of test strips that are intended to be stored at room temperature in closed cans provided with desiccant or moisture-impermeable foils, the degradation reaction should not occur or only to a very slight extent under these storage conditions.

The on-board control should in particular detect the following as incorrect storage:

high temperatures in closed cans/foils (e.g., during transport to the customer or behind a pane of glass in sunlight); and humid storage (cans that have not been properly closed after removing test strips or defective foil packaging).

These requirements were simulated by the following stress models:

Storage for several weeks at 50° C. in closed cans.

Storage for hours and several days at 50° C. and elevated (50%/75%) air humidity.

Storage for several days in an open or defective packaging under environmental conditions of climate zone 4 (30° C., 70% air humidity).

Figure 1:
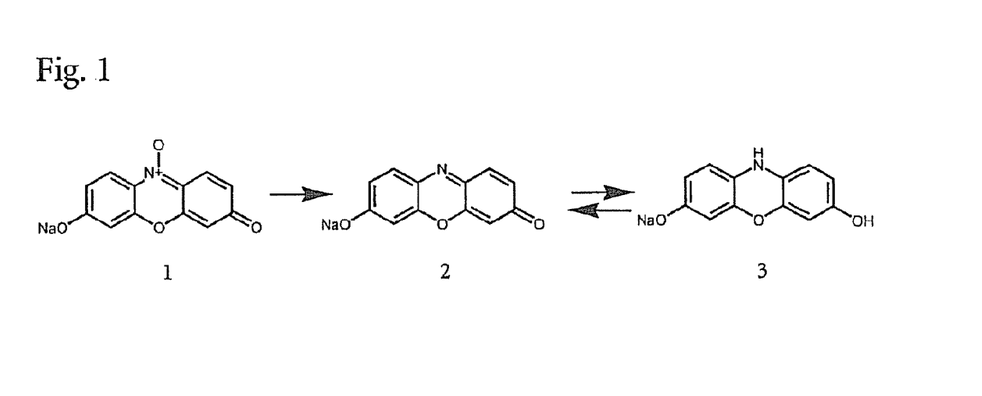
FIG. 1 shows the structural formulae of resazurin 1 which is converted by reduction into resorufin 2 and by further reduction into dihydro-resorufin 3.

The mass spectrum of a stressed reagent formulation which was prepared according to Table 1 in Example 1 shows that after stress (6 hours at 50° C. and 75% relative air humidity) a few percent of the resazurin was converted into resorufin (cf. also FIG. 1). The main peak of the resorufin spectrum (212.20 mass units) is present in addition to the main peak of the mass spectrum of resazurin at 228.17 mass units.

Example 3

Figure 2:
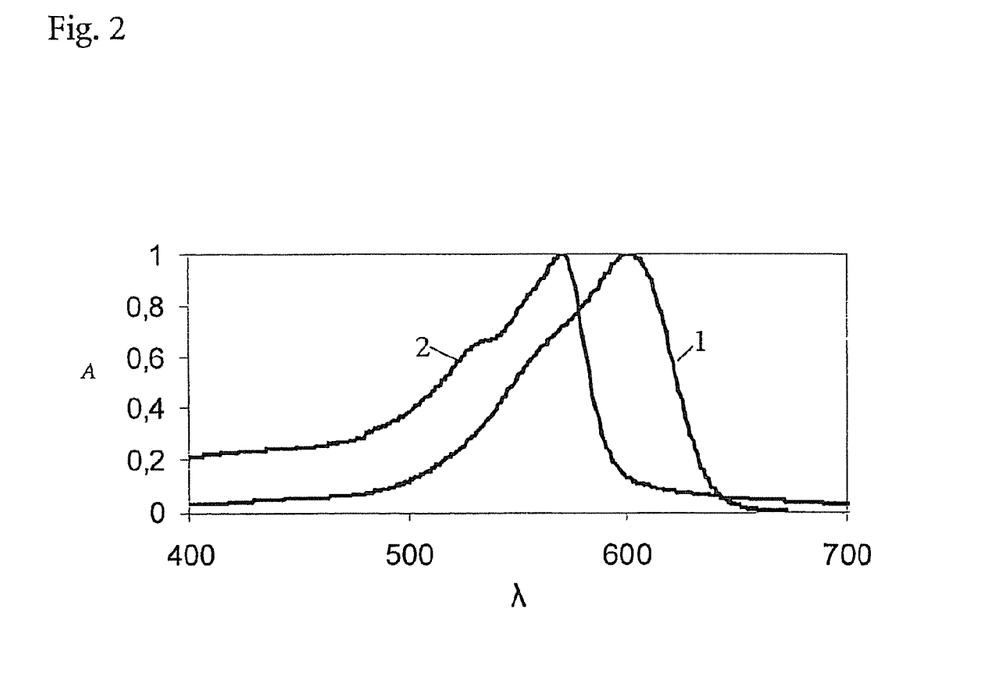
FIG. 2 shows absorption spectra (relative absorption A plotted versus the wavelength $\lambda$ (in nm)) of resazurin 1 and resorufin 2.

Absorption Spectra of Resazurin and Resorufin (FIG. 2)

The absorption spectra shown in FIG. 2 of resazurin 1 (a blue dye) and resorufin 2 (a red dye) show that in principle it is possible to optically detect (e.g., visually or by reflection photometry) the conversion of resazurin 1 into resorufin 2 which occurs when a reagent formulation is stressed as shown in Example 2.

Example 4

Reflection Spectra of Unstressed and Stressed Test Strips

Figure 3:
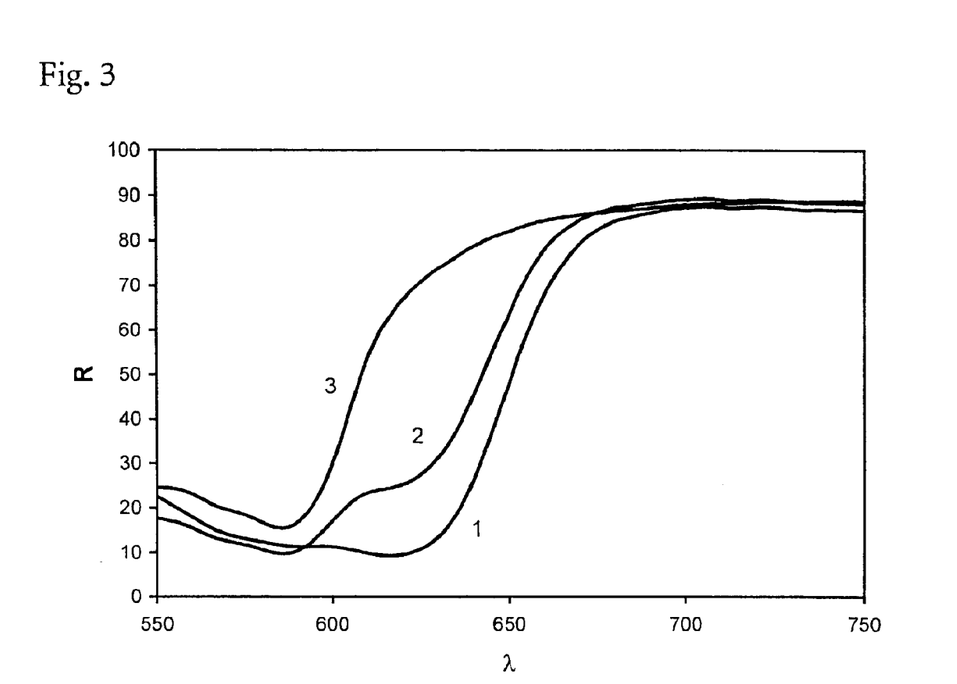
FIG. 3 shows the reflectance spectra (relative reflectance R (in %) plotted versus the wavelength $\lambda$ (in nm)) of the reagent fields of test elements that have been stressed to different extents (1 unstressed, 2 slightly stressed, 3 strongly stressed)

Test strips whose reagent films were prepared based on the formulation of Table 1 from Example 1 were stressed for 0 hours (unstressed; cf. curve 1 in FIG. 3), 6 hours (slightly stressed; cf. curve 2 in FIG. 3) and 12 hours (strongly stressed; cf. curve 3 in FIG. 3) at 50° C. and 75% air humidity. The change in the corresponding reflectance spectra was measured (FIG. 3). With an increase in stress, an increase in the reflectance at a wavelength of 620 nm is seen which is associated with a decrease in the amount of resazurin.

Example 5

Optical Detection of the Degradation Product Resorufin in Test Strips that were Stressed to Different Extents Test strips whose reagent films were prepared on the basis of the formulation of Table 1 from Example 1 were stressed for different periods at 50° C. and 75% air humidity and then measured in a simple reflection photometer whose LED operated with light at a wavelength of 620 nm.

Figure 4:
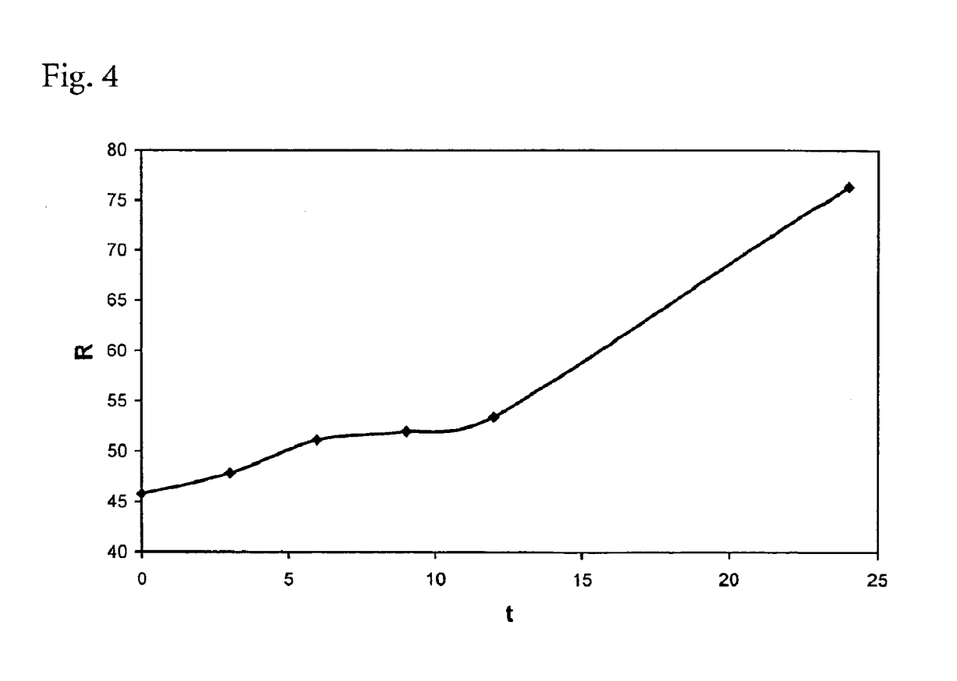
FIG. 4 shows the increase in degradation product (resorufin) in a resazurin-containing reagent film based on the increase of the relative reflectance R (in %) (measured at a wavelength of 620 nm) over the stress time t (in h)

FIG. 4 shows the increase in the degradation product (recognizable by the increase in reflectance R) over the stress time t (in h).

The change in the test field can also be readily detected visually i.e., by the user with the naked eye. The reagent zone of the unstressed test strip which is firstly blue changes its colour into pink as the stress period increases.

Example 6

Formulation for a PT Coagulation Test with Integrated OBC and Electrochemical Detection

TABLE 3

Formulation for an amperometric prothrombin time test with integrated OBC reagents

| Chemical | Source | Concentration |
| --- | --- | --- |
| relipidated recombinant human thromboplastin (rhTF) | Dade Behring, Marburg | 72 ng/ml |
| Sucrose | Sigma | 3.2 g/dl |
| mowiol 4/86 | Clariant GmbH | 1.3 g/dl |
| Keltrol F | Kelco | 2.98 g/ml |
| Glycine | Sigma | 1.35 g/dl |
| Polybrene | Sigma | 10 µg/ml |
| HEPES[1] | Sigma | 0.33 mg/ml |
| polyethylene glycol PEG 3,350 | Sigma | 1.33 g/dl |
| bovine serum albumin | Sigma | 0.4 g/dl |
| mega 8 | Sigma | 0.67 mg/ml |
| Resazurin | Riedel de Haen | 0.96 mg/ml |
| Electrozym TH | Roche Diagnostics | 1.2 mg/ml |

[1]HEPES: [4-(2-hydroxyethyl)-piperazino]-ethanesulfonic acid

The substances listed in Table 3 were homogeneously mixed and adjusted with NaOH to a pH of 7.4. The reaction mass obtained in this manner was coated in a width of 4 mm and a thickness of ca. 90 µm (wet) or ca. 10 µm (dry) on a test strip that is to be measured amperometrically such that the whole area of the working electrode was covered with reagent. An Ag/AgCl electrode which also served as the counter-electrode was used as a reference electrode.

Example 7

Electrochemical Detection of Resazurin and the Degradation Product Resorufin in Test Strips that were Stressed to Different Extents The test strips prepared according to Example 6 were stressed for different periods at 50° C. and 75% air humidity. Whole blood was then measured amperometrically with these test strips.

The following potentials were applied in order to quantify resazurin and resorufin:

−700 mV vs. Ag/AgCl for 3 seconds (so-called OBC prepare phase); subsequently

−100 mV vs. Ag/AgCl for 1.5 seconds (so-called OBC test phase); subsequently

+200 mV vs. Ag/AgCl for 90 seconds (for the actual coagulation measurement).

Figure 5:
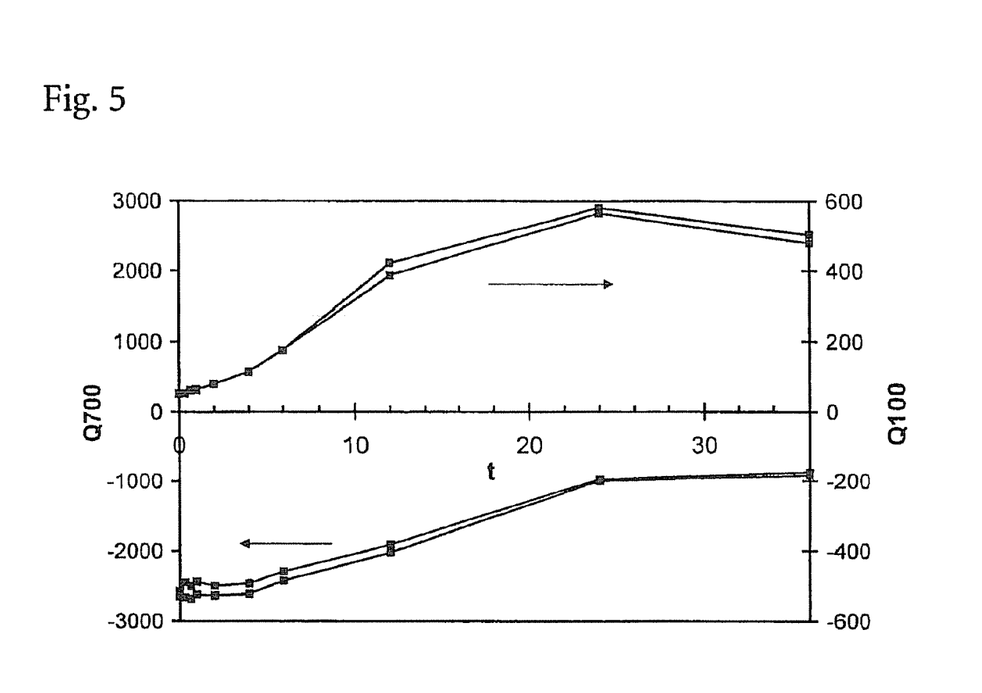
FIG. 5 shows the change of the signal that can be measured electrochemically during a first measuring phase lasting for 3 seconds at −700 mV versus Ag/AgCl ($Q_{700}$) (lower two curves) and a second measuring phase lasting for 1.5 seconds at −100 mV versus Ag/AgCl ($Q_{100}$) (upper two curves) on the basis of the dependence of the measured charge Q on the stress time t (in h).

In order to quantify the "OBC prepare" and "OBC test" signals, the integrals under the current-time curves were calculated. FIG. 5 shows how these integrals (referred to as $Q_{700}$ and $Q_{100}$) change with an increasing stress of the test strips.

Whereas there is a major change in the OBC signals, the clotting time measured with stressed test strips is almost stable up to a very long stress period (cf. Table 4).

TABLE 4

Effects of stress at 50° C. and 75% relative air humidity on the measurement of clotting time

| Stress time (h) | Clotting time (s) |
|---|---|
| 0 | 12.78 |
| 0.33 | 12.38 |
| 0.66 | 12.72 |
| 1 | 13.14 |
| 2 | 12.52 |
| 4 | 13.53 |
| 6 | 13.26 |
| 12 | 12.78 |
| 24 | 13.16 |
| 36 | 14.00 |

This ensures that the OBC indicates improper storage of the test strips before false clotting times are generated.

Example 8

Indication of the OBC with Electrochemical Detection when Unpackaged Strips are Stored in Climate Zone IV The greatest risk of damaging test strips whose packaging is defective or has not been closed again is in the case of customers that live in climate zone IV (hot and humid). For this climate zone a humidity of 70% and a temperature of 30° C. have been described in the literature as "average climate conditions".

Table 5 shows that the OBC with electrochemical detection indicates changes in the test strip due to storage under these conditions.

Table 5 shows on the basis of the measured charge Q (in nAs) versus the stress time t (in h) the change in the electrochemically measurable signal during a 3 second measuring phase at −700 mV vs. Ag/AgCl ($Q_{700}$) and during a 1.5 second measuring phase at −100 mM vs. Ag/AgCl ($Q_{100}$) for different sample materials (normal blood (N) 1 and 2; blood from donors that had been treated with Marcumar (M) 1 and 2).

TABLE 5

Effects of a stress at 30° C. and 70% relative air humidity on the electrochemical on-board control for different sample materials

| | $Q_{100}$ (nAs) | | | | $Q_{700}$ (nAs) | | | |
|---|---|---|---|---|---|---|---|---|
| t (h) | N 1 | N 2 | M 1 | M 2 | N 1 | N 2 | M 1 | M 2 |
| 0 | 58.42 | 57.3 | 51.7 | 56.8 | 2663 | 2512 | 2580 | 2735 |
| 2 | 58.62 | 57.9 | 56.0 | 58.0 | 2779 | 2551 | 2619 | 2748 |
| 6 | 62 | 62.0 | 62.3 | 63.6 | 2673 | 2567 | 2568 | 2728 |
| 9 | 62.21 | 61.4 | 61.0 | 63.8 | 2644 | 2466 | 2535 | 2713 |
| 12 | 65.16 | 63.4 | 61.7 | 65.8 | 2637 | 2488 | 2480 | 2723 |
| 24 | 77.07 | 76.0 | 75.6 | 78.8 | 2608 | 2455 | 2485 | 2722 |
| 48 | 94.56 | 89.0 | 84.4 | 89.2 | 2622 | 2493 | 2526 | 2665 |
| 72 | 102.3 | 104.3 | 100.1 | 105.2 | 2615 | 2455 | 2545 | 2705 |
| 96 | 119 | 123.7 | 122.1 | 127.5 | 2575 | 2466 | 2479 | 2722 |
| 120 | 151 | 141.8 | 145.0 | 167.2 | 2491 | 2434 | 2467 | 2535 |

Thus "stressed" analytical elements can be identified on the bases of measurement data which were obtained during the so-called OBC prepare phase (cf. Example 7) as well as during the so-called OBC test phase (cf. Example 7).

As shown in Table 6, the clotting times are also much more stable under these conditions and hence stressed test strips can be reliably detected by the OBC before false coagulation measurement values would have possibly been generated.

TABLE 6

Effects of stress at 30° C. and 70% relative air humidity on the measurement of clotting time

| Stress time (h) | Clotting time (s) |
|---|---|
| 0 | 11.66 |
| 2 | 11.94 |
| 6 | 12.28 |
| 9 | 12.14 |
| 12 | 12.27 |
| 24 | 11.82 |
| 48 | 11.88 |
| 72 | 11.66 |
| 96 | 11.63 |
| 120 | 11.67 |

Example 9

Glycine as a Specific Redox Partner for Resazurin

If test elements which contain the formulation from Example 6 are stored for 48 hours at 25° C., the ratio of resazurin to resorufin changes because the former is converted into the latter due to the "OBC reaction". The following Table 7 shows that the reaction rate of this reaction is influenced by the presence or absence of glycine. An OBC is also possible in the absence of glycine; however, the sensitivity of the OBC is considerably increased by the presence of glycine.

TABLE 7

Relative amount of resorufin (%) in relation to the total amount of resorufin and resazurin versus the stress period

| | Resorufin percentage (%) | |
|---|---|---|
| Stress period (h) | Reagent without glycine | Reagent with glycine |
| 0 | 5 | 10 |
| 0.5 | 6 | 16 |

TABLE 7-continued

Relative amount of resorufin (%) in relation to the total amount of resorufin and resazurin versus the stress period

| Stress period (h) | Resorufin percentage (%) | |
| --- | --- | --- |
| | Reagent without glycine | Reagent with glycine |
| 1 | 7 | 21 |
| 3 | 8 | 27 |
| 6 | 8 | 41 |
| 9 | 10 | 52 |
| 18 | 12 | 72 |
| 24 | 14 | 89 |
| 48 | 24 | 89 |

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. An analytical element comprising:
a first reagent system for a detecting an analyte, and
an on-board control comprising a second reagent system comprising an organic N-oxide or a nitroso compound and a reducing agent wherein the control produces a signal independent of the presence of the analyte as a result of reduction of the organic N-oxide or the nitroso compound by the reducing agent.

2. The analytical element of claim 1, wherein said second reagent system determines whether at least one of the analytical element, the first regent system and the second reagent system has been stressed under conditions that could damage the analytical element or affect results obtained therefrom.

3. The analytical element of claim 1, wherein the signal produced by the second reagent system can be detected optically or electrochemically.

4. The analytical element of claim 1, wherein the reducing agent is glycine or glucose.

5. The analytical element of claim 1, wherein the N-oxide is resazurin.

6. The analytical element of claim 1, wherein the nitroso compound is a substituted p-nitrosoaniline.

7. The analytical element of claim 1, wherein the second reagent system is integrated into the first reagent system.

8. The analytical element of claim 1, wherein the first reagent system comprises reagents for determining coagulation parameters.

9. The analytical element of claim 1 further comprising a heteropoly acid in combination with said nitroso compound.

10. A method for the control of an analytical element as claimed in claim 1, comprising detecting the signal from the second reagent system optically or electrochemically with the aid of a measuring instrument, wherein the signal indicates a stress of the analytical element.

11. The method of claim 10, wherein the analytical element for which a stress has been detected is not released by the measuring instrument for measurement of a sample liquid with the aid of the first reagent system.

12. The method of claim 10, wherein the signal produced by the second reagent system and a signal produced by the first reagent system are detected optically.

13. The method of claim 10, wherein the signal produced by the second reagent system and a signal produced by the first reagent system are detected electrochemically.

14. The method of claim 10, wherein the signal produced by the second reagent system is detected optically and a signal produced by the first reagent system is detected electrochemically.

15. The method of claim 10, wherein the signal produced by the second reagent system is detected electrochemically and a signal produced by the first reagent system is detected optically.

* * * * *